United States Patent [19]

Goel

[11] Patent Number: 4,512,927

[45] Date of Patent: Apr. 23, 1985

[54] NAPHTHYL ESTERS FROM TETRALIN

[75] Inventor: Anil B. Goel, Worthington, Ohio

[73] Assignee: Ashland Oil, Inc., Ashland, Ky.

[21] Appl. No.: 504,701

[22] Filed: Jun. 15, 1983

[51] Int. Cl.³ .............................................. C09F 5/08
[52] U.S. Cl. ................... 260/410.5; 260/410; 260/413; 560/131; 560/139
[58] Field of Search ..................... 260/413, 410.5, 410; 560/139, 254, 255, 131

[56] References Cited

U.S. PATENT DOCUMENTS

| | | | |
|---|---|---|---|
| 3,156,662 | 11/1964 | Dimmig et al. | 260/410.5 X |
| 3,493,605 | 2/1970 | Selwitz | 260/410.5 X |
| 3,542,852 | 11/1970 | Selwitz | 260/410.5 X |
| 3,547,982 | 12/1970 | McKeon | 260/410.5 X |
| 3,646,111 | 2/1972 | Hörnig et al. | 560/131 |
| 3,651,127 | 3/1972 | Hörnig et al. | 260/410.5 X |
| 3,772,383 | 11/1973 | Kominami et al. | 260/410.5 |
| 3,809,715 | 5/1974 | Hanotier et al. | 560/139 |
| 4,229,587 | 10/1980 | Murib | 260/410.5 X |
| 4,244,881 | 1/1981 | Giordano et al. | 260/410.5 |
| 4,464,303 | 8/1984 | Goel | 260/410.5 X |

Primary Examiner—Helen M. S. Sneed
Attorney, Agent, or Firm—John F. Jones

[57] ABSTRACT

A process for the preparation of naphthyl or indene carboxylates by reaction of tetralin or indane with oxygen and a carboxylic acid in the presence of a catalyst comprising palladium is described.

8 Claims, No Drawings

NAPHTHYL ESTERS FROM TETRALIN

This invention relates to the production of naphthyl esters from tetralin and more particularly pertains to the process for preparing naphthyl carboxylates by the reaction of tetralin with oxygen and a carboxylic acid in the presence of a palladium containing catalyst.

According to the prior art tetralin has been converted to tetralol and tetralone which can subsequently be converted to alpha-naphthol. See U.S. Pat. Nos. 3,354,231; 3,378,591; 3,105,018; 3,356,743; and 3,890,397, for instance. The separation of tetralone and tetralol from alpha-naphthol is difficult and requires special treatment. The direct conversion of tetralin to naphthyl esters in accordance with my invention has not been previously described. The naphthyl esters, of course, are useful themselves or as naphthol precursors. The hydrolysis of naphthyl carboxylates by known means produces the corresponding carboxylic acid and naphthol as is well known to those skilled in the art.

I have discovered a single step process for converting tetralin to naphthyl esters which can be further converted to the corresponding naphthols if desired. In accordance with my process, tetralin or similar compounds such as indane, tetrahydroanthracene, and the like are treated with oxygen or an oxygen containing gas and a carboxylic acid in the presence of a palladium catalyst at a temperature in the range of from 100° to 300° C. and preferably in the range of from 120° to 200° C. and at a pressure in the range of from 1 to 50 atmospheres, preferably in the range of from 1 to 5 atmospheres. The use of an inert organic solvent is also within the scope of my invention. The oxygen used in my process can be diluted with inert gas. Air is a convenient source of oxygen.

Organic solvents which may be used in my process preferably are those which will form azeotropic mixtures with water and thus will facilitate removal of water from the reaction mixture during the course of the reaction. Such solvents include linear and cyclic hydrocarbons, ethers, etc.

The palladium catalysts useful in my process are those of the type Pd/Sb/M wherein M is at least one member selected from the group consisting of K and Cr. Preferred catalysts for my process are carboxylate salts of the metals Pd, Sb and M such as palladium acetate, antimony acetate, potassium acetate and chromium acetate. The molar ratio of Pd:Sb:M in the catalysts of my invention can vary from 1:0.1:0.1 to 1:50:50. Preferably the molar ratio should be in the range of from 1:0.2:0.2 to 1:20:20.

The carboxylic acids useful in my process are those having from 2 to 19 carbon atoms. The oxidation of tetralin to the alpha-naphthyl ester proceeds rapidly and to essentially quantitative conversions when higher boiling carboxylic acids (such as octanoic acid) are used. When lower boiling carboxylic acids, e.g., acetic acid, are used the reaction usually proceeds at a slower rate.

The process of my invention is further illustrated in the following Examples.

EXAMPLE 1

A reactor equipped with mechanical stirrer, a thermometer with temperature controller to maintain nearly constant reaction temperature, a Dean Stark type collector with a condenser, and an oxygen inlet line was charged with 41 g. (284 millimols) of octanoic acid, 10.5 g. (79 millimols) of tetralin (tetrahydronaphthalene), 0.16 g. (0.71 millimols) of $Pd(OAc)_2$, 0.42 g. (1.42 millimols) of $Sb(OAc)_3$, 0.07 g. (0.71 millimols) of KOAc and 8 g. of n-heptane. The reaction mixture was stirred vigorously and oxygen was bubbled through it at the rate of 50–100 cc/min. during the entire reaction. The reaction temperature was about 160° C. and a reaction time of 3 hours was used. The water produced in the reaction was removed azeotropically with the refluxing heptane and was collected in the Dean Stark tube. Analysis of the reaction mixture at the end of the reaction showed that more than 99% of the starting tetralin had been converted to alpha-naphthyl octanoate.

EXAMPLE 2

The procedure of Example 1 was repeated except that 0.16 g. (0.71 m mols) of $Cr(OAc)_3.H_2O$ was used instead of the KOAc and the reaction was carried out at about 165° C. for 4 hours. A nearly quantitative conversion of tetralin with a selectivity of greater than 99% was achieved in this reaction.

EXAMPLE 3

The procedure of Example 2 was followed except that hexanoic acid (33 g.; 284 m mols) was used in place of octanoic acid and the reaction time was $3\frac{1}{2}$ hours. Analysis showed that about 55% of the tetralin was converted producing naphthyl hexanoate in 62% selectivity.

EXAMPLE 4

The procedure of Example 1 was repeated using 70 g (304 mmols) of dodecanedioic acid 13.2 g (100 mmols) of tetralin, 0.16 g (0.71 mmols) of $Pd(OAc)_2$, 0.42 g (1.42 mmols) of $Sb(OAc)_3$, 0.07 g (0.71 mmols) of KOAc and 5 ml heptane. Reaction mixture was heated and the temperature of the reaction was maintained at 178±2° C. Oxygen was bubbled continuously at a rate of 200 cc/min. Reaction was carried out for 3 hrs. during which time the water produced was removed azeotropically with heptane. Reaction mixture was analyzed by GLC which showed the formation of 3.65% (by wt.) naphthyl dodecanedioate. Only a trace of naphthalene formed in the reaction.

EXAMPLE 5

The procedure of Example 1 was followed except that 10 g of indane was used instead of tetralin. The reaction was carried out for 3 hours. The GLC analysis of the mixture revealed that about 32% of the indane was converted to octanoxy indene.

I claim:

1. The process for preparing a member selected from the group consisting of naphthyl carboxylate and an indene carboxylate consisting essentially of reacting tetralin or indane respectively with oxygen and a carboxylic acid having from 2 to 19 carbon atoms at a temperature of from 120° C. to 200° C. in the presence of a catalyst which contains the elements Pd/Sb/M wherein M is at least one member selected from the group consisting of K and Cr.

2. The process of claim 1 wherein the catalyst is a carboxylate of each element Pd, Sb and M.

3. The process of claim 2 wherein the catalyst is composed of palladium acetate, antimony acetate and potassium acetate and the carboxylic acid is octanoic acid.

4. The process of claim 2 wherein the catalyst is composed of palladium acetate, antimony acetate and chromium acetate and the carboxylic acid is octanoic acid.

5. The process of claim 4 wherein the catalyst is composed of palladium acetate, antimony acetate and chromium acetate and the carboxylic acid is hexanoic acid.

6. The process of claim 2 wherein the catalyst is composed of palladium acetate, antimony acetate, and potassium acetate and the carboxylic acid is dodecane dioic acid.

7. The process of claim 3 wherein tetralin is used.

8. The process of claim 3 wherein indane is used.

* * * * *